United States Patent [19]
Harlow

[11] Patent Number: 5,445,601
[45] Date of Patent: Aug. 29, 1995

[54] BACK SUPPORT DEVICE HAVING BANDS SECURING THE SUPPORT PLATE

[75] Inventor: Robert R. Harlow, Humble, Tex.

[73] Assignee: TBC Orthopedics, Inc., Humble, Tex.

[21] Appl. No.: 233,293

[22] Filed: Apr. 26, 1994

[51] Int. Cl.$^6$ ............................ A61F 5/00; A61G 15/00
[52] U.S. Cl. ............................. 602/19; 2/44; 128/876; 128/845
[58] Field of Search ............... 2/44, 45, 918, 911, 2/908; 602/19; 128/876, 875, 869

[56] References Cited

U.S. PATENT DOCUMENTS

| | | |
|---|---|---|
| 421,635 | 2/1890 | Teufel . |
| 766,863 | 8/1904 | Adams . |
| 1,174,757 | 3/1916 | Packer ............... 602/19 |
| 2,029,557 | 2/1936 | Buckley . |
| 2,146,444 | 2/1939 | Roe . |
| 2,160,709 | 5/1939 | Peckham . |
| 2,733,712 | 2/1956 | Wuesthoff . |
| 2,871,850 | 2/1959 | Peckham . |
| 3,532,090 | 10/1970 | Ward et al. . |
| 3,889,664 | 6/1975 | Heuser et al. . |
| 4,175,553 | 11/1979 | Rosenberg ............... 2/44 |
| 4,245,628 | 1/1981 | Eichler ............... 602/19 |
| 4,384,372 | 5/1983 | Rector ............... 602/19 |
| 4,708,130 | 11/1987 | Grudem . |
| 5,040,524 | 8/1991 | Votel et al. ............... 602/19 |
| 5,127,897 | 7/1992 | Roller . |
| 5,147,261 | 9/1992 | Smith et al. ............... 602/19 |
| 5,179,942 | 1/1993 | Drulias et al. ............... 602/19 |
| 5,188,586 | 2/1993 | Castel et al. ............... 602/19 |
| 5,205,815 | 4/1993 | Saunders ............... 602/19 |
| 5,257,419 | 11/1993 | Alexander ............... 602/19 |
| 5,310,401 | 5/1994 | Striano ............... 2/44 |

FOREIGN PATENT DOCUMENTS 2687912 9/1993 France ............... 602/19

OTHER PUBLICATIONS

Direct Safety Co. 1994 Master Catalog, pp. 68–74.
Newspaper supplement ad for "Nu-Therapy Back Support."
Ad for Tru-Fit Industrial Back Support model Nos. 9283 & 9284.
Ad for Tru-Fit back support model No. 8941.

Primary Examiner—Robert A. Hafer
Assistant Examiner—Michael O'Neill
Attorney, Agent, or Firm—John R. Kirk, Jr.; Jenkens & Gilchrist

[57] ABSTRACT

A lower back support device for use in applying force to the lumbar vertebrae of the human spinal column. The device has a support plate attached to a pair of inner bands, for encircling the wearers' body to position the support plate. It also has a one-piece outer band, which fastens to its outside of the inner band to pass the plate toward the back of the wearer.

1 Claim, 6 Drawing Sheets

BACK SUPPORT DEVICE HAVING BANDS SECURING THE SUPPORT PLATE

BACKGROUND OF THE INVENTION

1. Field of the Invention

The present invention generally relates to a back support device, and more particularly to a belt with a back support plate for use in applying force to the lumbar vertebrae of the human spinal column.

2. Description of related Art

The skeleton, especially the skull, has figured importantly in human thought and imagination. Death has been. symbolized as a harvester, a skeleton carrying a scythe, who reaps all life. The skeleton remains, even after human flesh has decomposed, because the calcium and phosphorous compounds it contains do not easily decay.

The skeleton of the human consists of two major portions. The axial skeleton runs along the axis of the body and includes the skull, other bones in the head, the spinal column, ribs, and tailbone. The appendicular skeleton includes the bones in the limbs and in the girdles that attach the limbs to the spinal column; the pectoral girdle includes the collarbones and shoulder blades, And the pelvic girdle includes the large, fused hip bones.

While the bones in our bodies permit the locomotory muscles to perform their allotted tasks, they must serve many other functions as well. They provide a framework that supports the body against the pull of gravity. The bones of the spinal column and the pelvis carry most of the body weight, and permit upright standing and walking. Part of the skeleton also provides protection for delicate internal organs. The heart and lungs are well sheltered in the chest, the bones of the skull armor the brain, and the spinal column forms a bony canal surrounding the spinal column.

Despite its rigid framework, many parts of the skeleton are fragile and can be particularly troublesome. One of humankind's major medical problems involves various difficulties with the spinal column. The spinal column is a complicated body part—a stack of vertebrae cushioned by shock-absorbing discs, which are positioned between the individual vertebrae, surrounds a stem of nerves and is embedded in the center of a complex network of muscles and ligaments. Because of exertion, illness, accident, or abuse, one or more of these discs, or at least a portion of the discs, becomes ruptured or otherwise requires repair or, more often, removal.

At any given time, one out of eight people has some kind of back pain, according to one estimate. After the common cold, the common backache is the most popular reason for missing work. Most back pain results from cumulative deterioration, not a one-time action. Bending over to pick up something may be the straw that broke the camel's back, but poor posture will slowly pile on straws day after day, year after year.

Expensive high-tech imaging equipment, from x-rays to magnetic resonance imaging, often cannot detect the source of pain. Sometimes they can even throw a doctor off track. Because of this, more doctors are considering surgery only if necessary and are taking a sports medicine-like approach to treating back pain. That means tuning up, strengthening, and stretching the body instead of telling it to rest until the pain goes away. With the back in particular, everything we do, or don't do, has an impact. If our muscles are weak, the spine bears more of the weight burden, putting strain on the bones, discs, muscles, and ligaments. Poor posture and bad habits accelerate the natural degeneration of the spine.

So while back pain is one of the most common reasons for a visit to a doctor, it's one of the least understood. Various treatments and modalities have been used to treat back ailments. Osteopathic physicians and chiropractors frequently manipulate a portion of the spine to remedy back ailments. Such manipulation sometimes includes the applying of force and pressure to specific localized areas. It has been found advantageous to have such force directed at specific portions of the spine for periods of times which far exceed that normally associated with such manipulative therapy.

Prevention has now become popular to protect against the occurrence of a back injury. One means for applying force to the vertebrae of the spinal column is through wearing back support belts or braces. Today, it is common to see stockers in grocery stores or construction workers on the job site wearing a device to support the back during heavy lifting and repetitive motion situations. The supports are typically made of a woven material with a flexible core and are orthopedically designed to encourage proper lifting technique. Some of these devices are also used in a therapeutic setting, to be worn by individuals already suffering from troublesome back pain.

For example, U.S. Pat. No. 5,127,897 describes a therapeutic back support device having a pair of laterally spaced apart belts detachably coupled about the waist of the user via belt buckles. Mounted on the forward face of the back support plate is a vertical sliding support bar to which a pair of semi-spherical members is attached. While this device may provide localized force to any selected one of a plurality of different portions of the human spine along the length of the spine, it is cumbersome and unpleasant to wear. It is an object of the present invention to provide a back support device that supplies durable support while not sacrificing comfort and which is easy to adjust to provide variable degrees of tension to the lumbar region of the spinal column.

SUMMARY OF THE INVENTION

The present invention relates to a lower back support device for use in applying force to the lumbar vertebrae of the human spinal column. The device has a support plate, a two-piece inner band, a one-piece ouer band, and a pad. The support plate has a plurality of elongate vertical slots and is adapted to be positioned rearwardly adjacent the back. The two-piece inner band is adapted to extend around the body of the wearer and has a distal and proximal body side. The distal body side is covered with loop fastening means and the proximal body side is covered with a smooth material. The inner band also has means for attaching to the support plate. The one-piece outer band, which is adapted to extend at least partially around the body of the wearer, has a first and second end, each terminating in hook fastening means facing toward the body of the wearer. The outer band also has means for attaching to the support plate. The outer band is adjustably attached to the inner band by attaching the hook fastening means to the loop fastening means of the distal body sides of the inner band to urge the support plate against the back of the wearer.

BRIEF DESCRIPTION OF THE DRAWINGS

The accompanying drawings, which are incorporated in and form a part of the specification, illustrate the embodiments of the present invention, and, together with the description, serve to explain the principles of the invention. In the drawings.

It is to be noted that the drawings illustrate only typical embodiments of the invention and are therefore not to be considered limiting of its scope, for the invention will admit to other equally effective embodiments.

DETAILED DESCRIPTION OF THE INVENTION

The human back includes an upstanding spine having a plurality of vertically stacked vertebrae separated by vertebral discs. The seven upper most vertebrae are commonly known as the cervical vertebrae and make up the cervical spine. The next lower vertebrae are commonly known as the thoracic vertebrae and make up the thoracic spine. The next lower five vertebrae are commonly referred to as the lumbar vertebrae and make up the lumbar spine. The remaining portion of the spine is called the sacrum. The back support device of the present invention is made of lightweight materials that fit easily and comfortably, and is easily applied to the lumbar, lower lumbar, or lumbo-sacral part of the spine. The device is of simple construction and formed of readily obtainable materials to be economically feasible and can be adjusted to fit wearers of various sizes.

Figure 1:
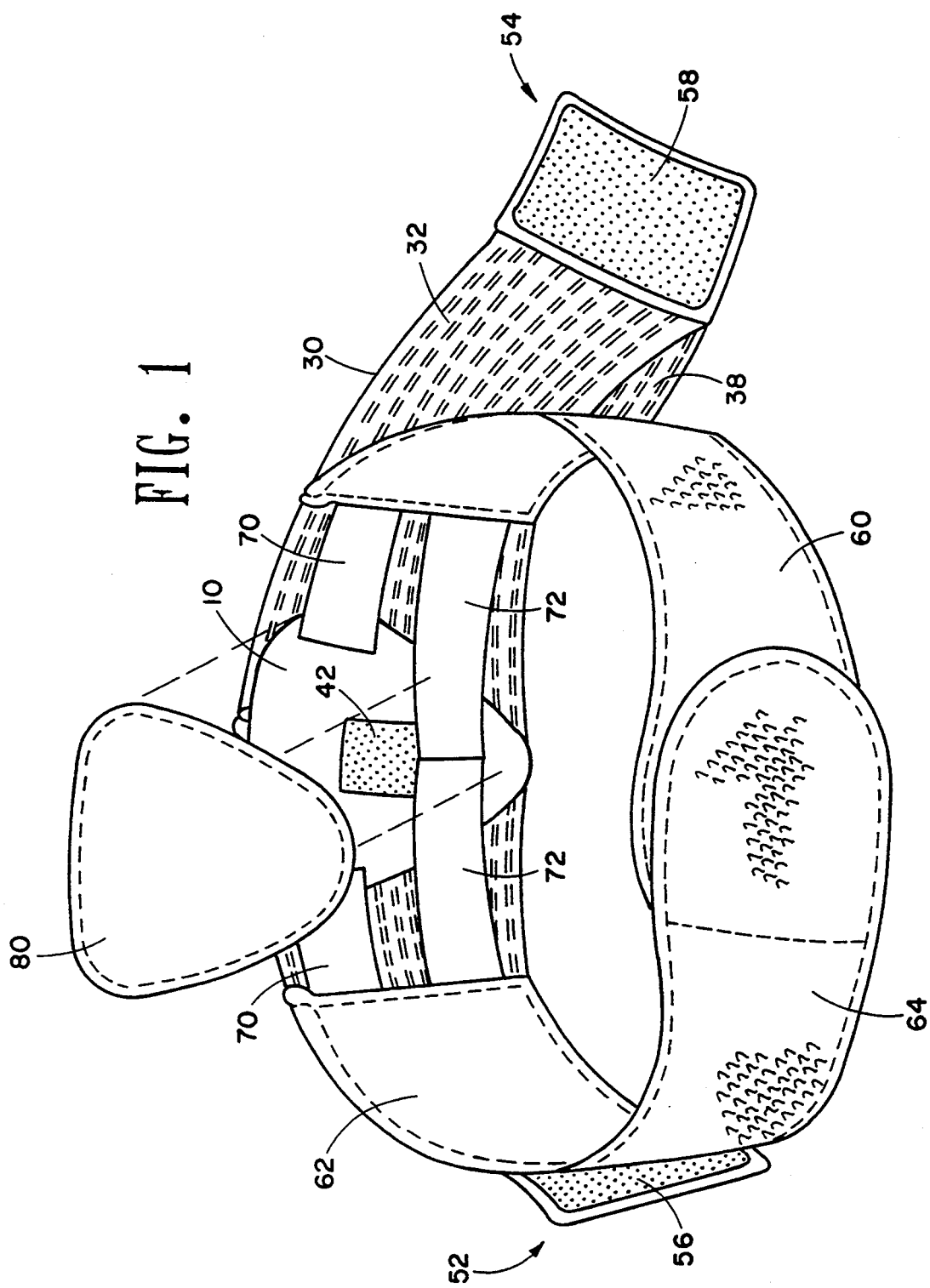
FIG. 1 is a perspective view of the assembled back support device of the present invention showing the support plate, two-piece inner band, one-piece outer band, and pad.

An embodiment of the back support device is shown in a perspective view in FIG. 1. Generally, the device comprises a belt having a support plate 10, a one-piece outer band 30, a two-piece inner band 60, and a pad 80. The support plate 10 has a predefined shape and is adapted to be positioned rearwardly adjacent the lumbar region of a human back. The support plate 10 has a plurality of elongate vertical slots 12a, 12b, 14a, 14b, and 16 (FIG. 2) formed therethrough to which the outer band 30 and the two-piece inner band 60 may be attached by hook and loop fastening means, commonly known as VELCRO brand fasteners. Outer band 30 is adapted to extend at least partially, under tension comfortable to the wearer, around the body of the wearer. Similarly, the inner band 60 is adapted to extend around the body of the wearer. The outer and inner bands may be made of nylon, mesh fabrics, woven elastic, spandex knit, or other resilient semi-flexible material and may be ventilated to provide cooling comfort in warm work environments. In addition, the back support device may have suspenders or shoulder straps permanently or removably attached to one or more of the bands.

Figure 2:
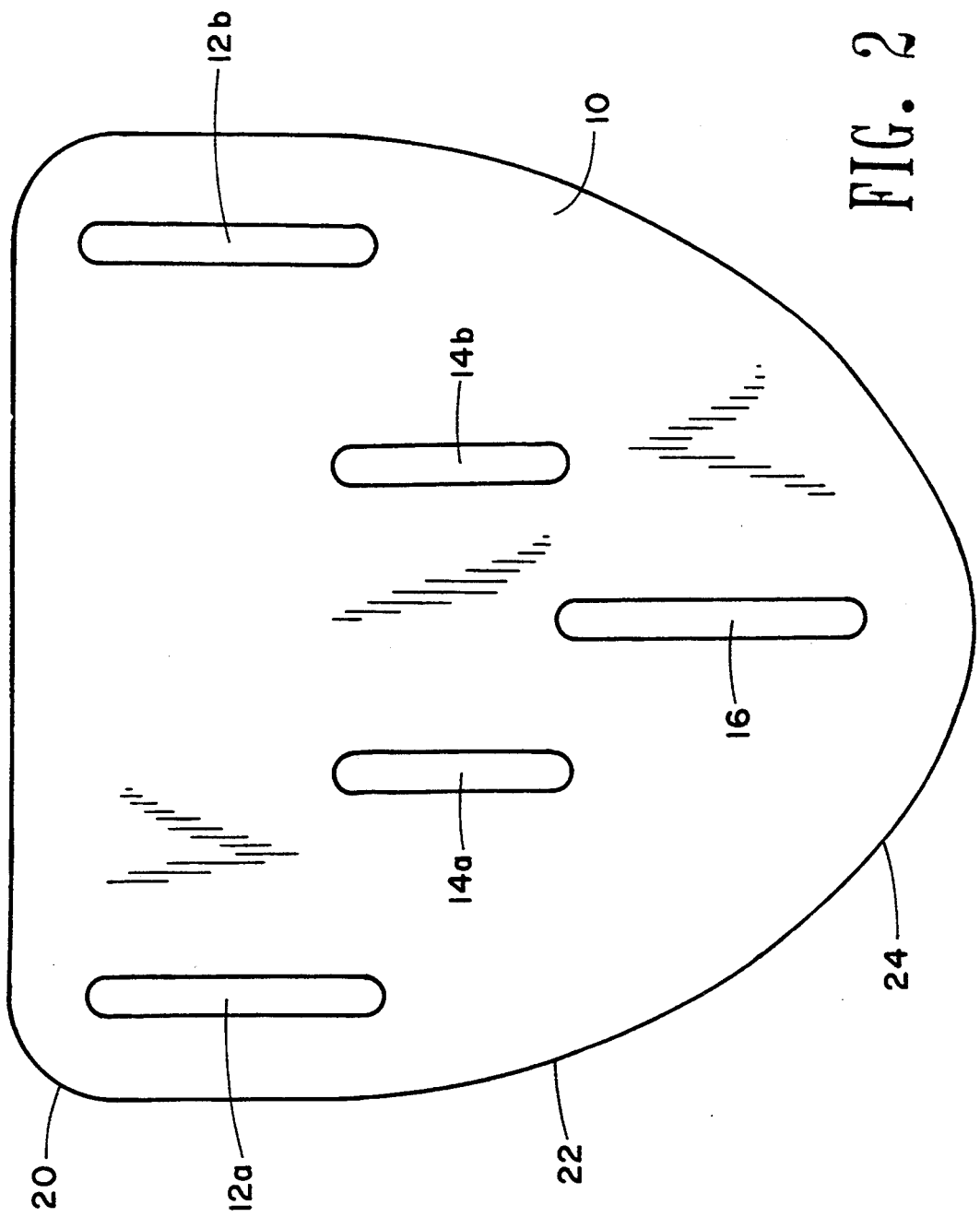
FIG. 2 is a front view of the support plate.

FIG.2 shows the support plate 10 having a plurality of elongate vertical slots (12a, 12b, 14a, 14b and 16). The vertical slots are constructed to receive tab 40 and elastic bands 70 and 72 as discussed below. The support plate 10 is curvilinear and includes upper portion 20 and lower portion 24 on vertically opposite ends of an intermediate portion 22. The upper portion 20 is wider than lower portion 24. Support plate 10 is constructed of firm, but yieldable, plastic material and is normally positioned at various portions of the lower spine of the wearer. The back support plate 10 is bent and flexed to fit snugly and nicely around the back side of the body of the wearer.

Figure 3:
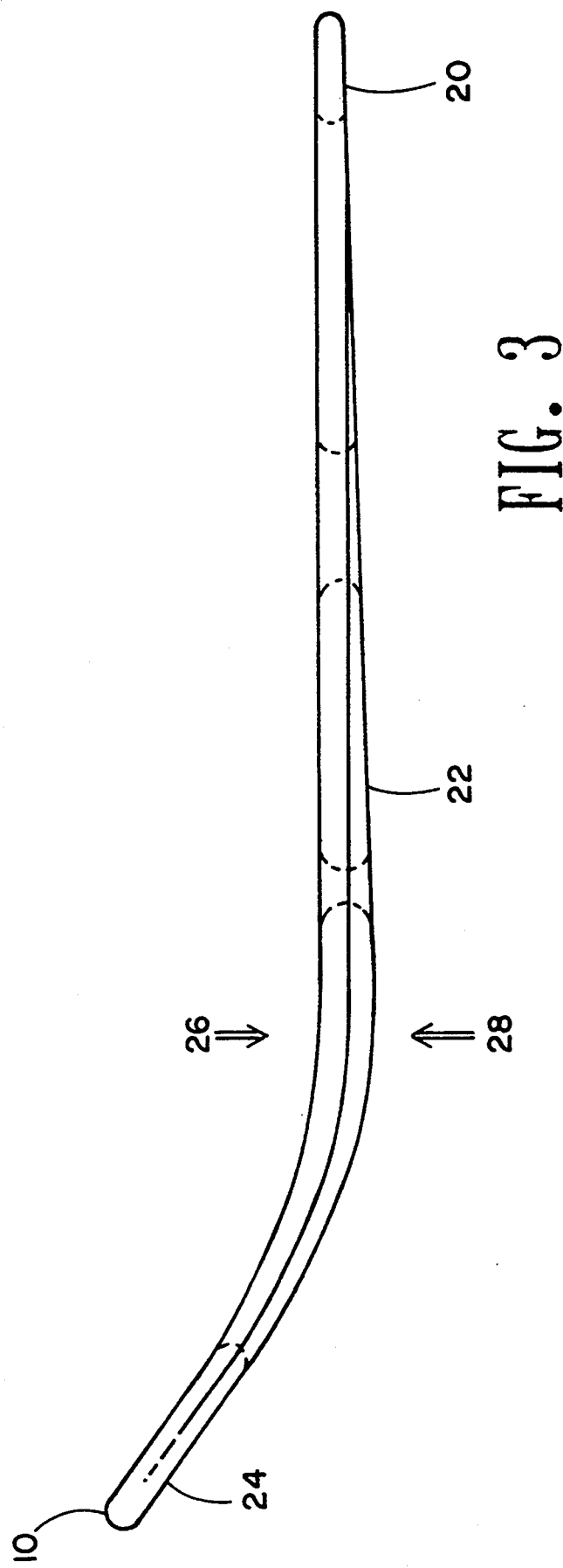
FIG. 3 is a side view of the support plate shown in FIG.2.

FIG. 3 shows the support plate 10 having a normal predetermined radius of curvature in an unstressed position such that the upper 20 and lower 24 portions are rearward of said intermediate 22 portion but being yieldable to allow said upper 20 and lower 24 portions to be moved forwardly relative to said intermediate 22 portion to a stressed position to increase the radius of curvature. FIG. 3. also shows the relative location of slots 12a and 12b, slots 14a and 14b, and slot 16. The proximal body side of the support plate 10 (indicated by 28 in FIG. 3) is positioned rearwardly adjacent the lumbar area of the human back. The distal body side of the support plate 10 is indicated by 26.

Figure 4:
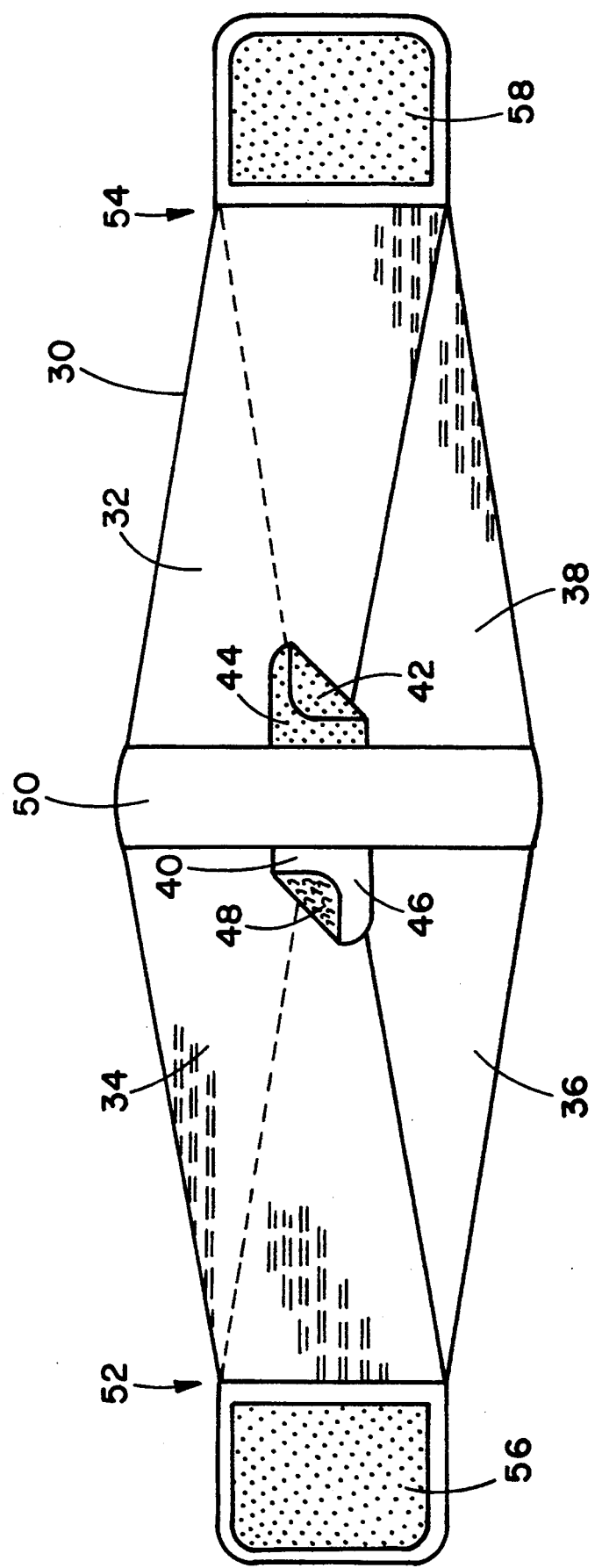
FIG. 4 is a front view of the proximal body side of the outer band.

Turning now to FIG. 4, there is shown a front view of the one-piece outer band 30. The outer band 30 is made of a resilient semi-flexible material adapted to extend at least partially, under tension comfortable to the wearer, around the body of the wearer. Generally, the outer band 30 is comprised of a plurality of rectangular members 32, 34, 36, and 38. In the preferred embodiment, the rectangular members of the outer band 30 are constructed of four inch vented elastic which provides a variable degree of tension. In this proximal body side view of FIG.4, rectangular members 32 and 34 overlap or cover rectangular members 36 and 38. Retaining strip 50 is positioned near the center of the outer band 30 and serves to join the rectangular members 32, 34, 36, and 38 at the proximate center of the outer band 30. The least amount of overlap between rectangular members 32 and 38 and likewise with rectangular members 34 and 36 is positioned at the retaining strip 50. In the preferred embodiment, the body-conforming design of the outer band 30 provides 7½ inch width coverage at the wearer's back and narrows to 5½ inch at the abdomen. Proceeding outwardly from the proximate center of the outer band, there are a first end 52 and a second end 54, respectively, each ending in hook fastening means 56 and 58 facing toward the body of the wearer.

FIG. 4 also shows tab 40 which is attached to the outer band 30 by the retaining strip 50. The tab 40 may be glued, sewn, or riveted directly to the outer band 30 or "sandwiched" between the strip 50 and band 30 and held in place when the strip 50 is glued, sewn, or riveted to the band 30. Side 42 of the tab 40 is covered with hook fastening means, as is side 44. Side 46 of the tab 40 is smooth, whereas side 48 is covered with loop fastening means. The outer band 30 is attached to the support plate 10 by the hook and loop fastening means of the tab 40 which is attached to the approximate center of the outer band 30. Sides 42 and 44 of the tab 40 are inserted through vertical slot 14b of the support plate 10. Sides 46 and 48 of the tab 40 are inserted through vertical slot 14a of the support plate 10. The hook and loop fastening means of tab 40 is adapted to encircle a portion of the support plate 10 extending between the pair of elongate vertical slots 14a and 14b such that side 48 is folded down over the support plate 10 in the direction of slot 14b to mate with side 44 of tab 40 which is folded down in the direction of slot 14a to hold the support plate 10.

Figure 5:
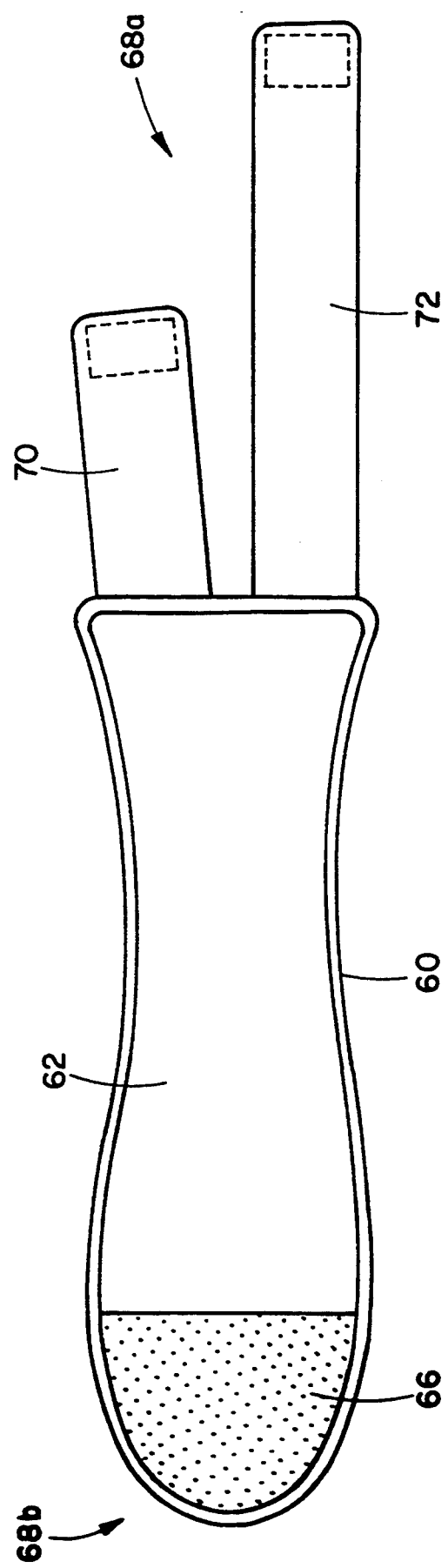
FIG. 5 is a front view of the proximal body side of an embodiment of an inner band.
Figure 6:
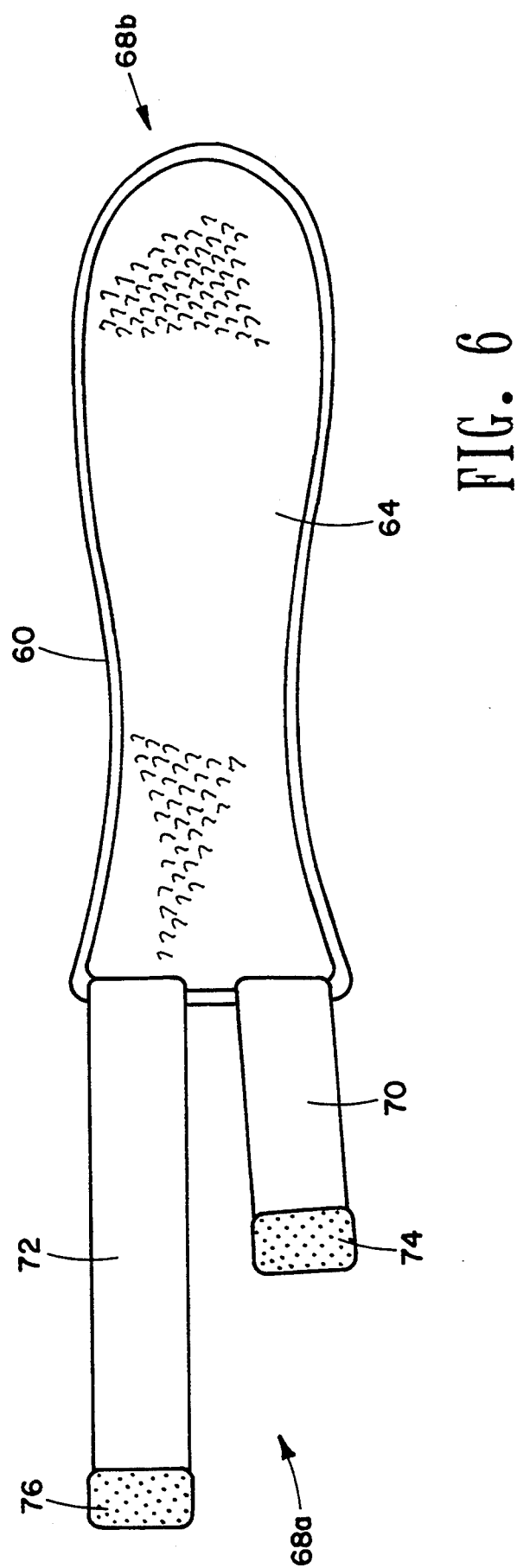
FIG. 6 is a front view of the distal body side of the inner band shown in FIG. 5.

FIG. 5. shows the proximal side and FIG. 6 shows the distal side of one piece of the two-piece inner band 60. The inner band 60 is comprised of a foam fabric material which is adapted to extend around the body of the wearer. Proximal body side 62 of the inner band 60 is covered with a smooth material, for example, a brushed tricot lining or similar material, for extra comfort. In contrast, the distal body side 64 of the inner band 60 is covered with loop fastening means. The inner band 60 has a first end 68a and a second end 68b. The first end 68a comprises a plurality of elastic bands 70 and 72, terminating in hook fastening means 74 and 76 on the distal body side. In the preferred embodiment, the inner band 60 has adjustable two-inch inner elastic bands 70 and 72 which assure precise sizing. The second end 68b of the proximal body side 62 of one piece of the inner band 30 comprises hook fastening means 66. The second piece (not shown) of the inner band 60 has a continuous smooth side 62. In essence, the second piece of the two-piece inner band 60 is the mirror image of the first piece.

As seen in FIG. 1, the inner band 60 is attached to the support plate 10 by threading the elastic bands 70 and 72 through slots 12b and 16 and slots 12a and 16 of the support plate 10. The terminating hook fastening means 74 and 76 mate with the loop fastening means covering the distal body side 64 of the inner band 60. Alternatively, the inner band 60 could be secured around the body of the wearer through the use of a strap or straps which are adjustably engageable with corresponding hook connection or connections, similar to an ordinary belt buckle.

To assemble the back support device of the present invention, the tab 40 of the outer band 30 is threaded through slots 14a and 14b and attached by the hook and loop fastening means. Then elastic bands 70 and 72 of one piece of the inner band 60 are threaded through slots 12b and 16 respectively and mated with the loop fastening means of side 64 of the inner band 60. Elastic bands 70 and 72 of the second piece of the two-piece inner band 60 are threaded through slots 12a and 16 and attached in a similar fashion. The back support device is positioned so that the support plate 10, with the upper portion 20 at the top, is centered directly over the lumbar area of the spine. If desired, a changeable foam pad 80 or a hot/cold gel-pak may be attached. The distal side of the pad 80 may be covered with loop fastening means to mate with side 42 of the tab 40 positioned at the proximate center of the support plate 10. To assure proper plate 10 alignment, ensure that the ends 68b of the inner band 60 are even in front of the body. Pull forward on the two pieces of the inner band 60 to stretch the inner elastic bands 70 and 72, which draws the support plate 10 firmly to your back. Hold the tension and wrap hook fastening means 66 over loop fastening means of side 64. The inner band 60 is now fastened firmly and properly around the body.

Pull the ends 52 and 54 of the outer band 30 to the desired tension and mate hook fastening means 56 to the loop fastening means of the distal side 64 of the inner band, and hook fastening means 58 to the loop fastening means 6f the distal side 64 of the inner band 60. The amount of pressure applied can be adjusted by merely moving the outer band ends 52 and 54 forward to increase the back support pressure and backward to decrease the back support pressure. If desired, the back support device of the present invention may be worn unobtrusively beneath the clothing. The invention thus allows relief without embarrassment and, as a result, many people who would not wear this type of device before will now take advantage of the beneficial treatment afforded thereby.

The above embodiments are given by way of example and are not intended as limitations as further embodiments and advances will occur to those skilled in the art which practice the present invention.

What is claimed is:

1. A lower back support device for treating lumbar vertebrae of a spine located in a back of a human body, comprising:

a firm plastic support plate having a predetermined radius of curvature and having an upper portion and a lower portion on vertically opposite ends of an intermediate portion such that said upper and lower portions are adapted to be positioned facing rearwardly with the intermediate portion adjacent the lumbar region of said human back and further having a plurality of elongate vertical slots formed therethrough for attaching bands to said plate;

a pair of foam fabric inner bands adapted to extend around the body of the wearer and each band having a distal body side, a portion of which is covered with loop fastening means, and a proximal body side, a portion of which is covered with a smooth material, and having a first and a second end, said first end of said distal body side comprising a plurality of elastic bands terminating in hook fastening means and said second end of said proximal body side of one piece of each inner band having hook fastening means, and each inner band being attachable to said support plate in response to threading said elastic bands of each inner band through said slots of said support plate, wherein said terminating hook fastening means of said first end attach to said loop fastening means of said distal body side; and a one-piece resilient semi-flexible outer band adapted to extend at least partially, under tension comfortable to the wearer, around the body of the wearer, and having a first and a second end, each terminating in hook fastening means facing toward the body of the wearer, and being attachable to said support plate by hook and loop fastening means being connected to the proximate center of said outer band, wherein said fastening means is adapted to encircle a portion of said support plate extending between a pair of elongate vertical slots of said support plate, and said outer band adjustably attachable to each inner band by contacting said hook fastening means of said outer band ends to said loop fastening means of said distal body sides of each inner band to provide comfortable tension to urge said support plate against the back of the wearer.

* * * * *